United States Patent [19]

Witte et al.

[11] Patent Number: 4,599,305
[45] Date of Patent: Jul. 8, 1986

[54] METHOD AND COMPOSITION FOR DETECTION OF HUMAN CHRONIC MYELOGENOUS LEUKEMIA

[75] Inventors: Owen N. Witte; Susan Watanabe; James Konopka, all of Santa Monica, Calif.

[73] Assignee: The Regents of the University of California, Berkeley, Calif.

[21] Appl. No.: 631,233

[22] Filed: Jul. 16, 1984

[51] Int. Cl.$^4$ .................... G01N 33/53; C12N 15/00
[52] U.S. Cl. ................... 435/7; 435/172.3; 435/235; 435/6; 436/536; 436/538; 436/547; 436/804; 436/813; 436/823; 935/47; 935/60; 935/27; 530/387; 530/806; 530/329; 530/327; 530/326
[58] Field of Search ................ 436/514–516, 436/536–542, 543–548, 804, 811, 813, 815, 823; 435/4, 5, 6, 7, 235–239, 317, 172, 391, 820, 948; 424/1.1, 9, 85, 86, 77; 260/112 R; 935/9, 12, 27, 47, 56, 60

[56] References Cited

U.S. PATENT DOCUMENTS

| | | | |
|---|---|---|---|
| 4,100,022 | 7/1978 | Ogasa et al. | 195/1.8 |
| 4,323,546 | 4/1982 | Crockford et al. | 424/1.1 |
| 4,364,936 | 12/1982 | Kung et al. | 424/85 |
| 4,379,839 | 4/1983 | Spiegelman | 435/5 |

OTHER PUBLICATIONS

Dale, B. et al., UCLA Symp. Mol. Cell. Biol. 5 in *Tumor Viruses & Differentiation*, Scolnick, E. M. et al. ed, Liss, NY (1983).
Groffen, J. et al., *Nature*, vol. 304, pp. 167–169, (1983).
Reynolds, F. H. et al., *J. Virology*, vol. 44(3), pp. 1097–1101, (1982).
Canaani, E., *Lancet* vol. 1 (8377), pp. 593–595, (1984).
Collins, S. J. et al., *Science*, vol. 225 (4657), pp. 72–74, (1984).
Collins, S. J. et al., *Proc. Natl. Acad Sci, USA*, vol. 80, pp. 4813–4817, (1983).
Witte, O. N. *Current Topics in Microbiology*, vol. 103, pp. 127–146, (1983).
Ponticelli, A. S. et al., *Cell*, vol. 29(3), pp. 953–960 (1982).
Bartram, C. R. et al., *Nature*, vol. 306, pp. 277–280, (11-1983).
Wang, J. Y. J. et al., *Cell*, vol. 36, pp. 349–356, (12-1984).
Heisterkamp, N. et al., *Nature*, vol. 306, pp. 239–242, (11-1983).
Whitlock, C. A. et al., *Cell*, vol. 32, pp. 903–911 (3-1983).
Jane, M. et al., *Nature*, vol. 300(5893), pp. 659–661 (12-1982).
Mushinski, J. F. et al., *Science*, vol. 220 (4599), pp. 795–798, (5-1983).
Reddy, E. P. et al., *Proc. Natl. Acad. Sci, USA*, vol. 80, pp. 3623–3627, (6-1983).
DeKlein, A. et al., *Nature*, vol. 300(5894), pp. 765–767, (12-1982).
Heisterkamp, N. et al., *Nature*, vol. 299(5885), pp. 747–749 (10-1982).
Whitlock, C. A. et al., *Molecular & Cellular Biology*, vol. 3,(4), pp. 596–604, (4-1983).
Goff, S. P. et al., *Science*, vol. 218, pp. 1317–1319 (12-1982).
Konopa, J. B. et al., *Journal of Virology*, vol. 51(1), pp. 223–232, (Jul. 1984).
Konopa, J. B. et al., *Cell*, vol. 37, pp. 1035–1042 (Jul. 1984).

*Primary Examiner*—Alvin E. Tanenholtz
*Assistant Examiner*—M. Moskowitz
*Attorney, Agent, or Firm*—Poms, Smith, Lande & Rose

[57] ABSTRACT

A method for detecting chronic myelogenous leukemia in a human comprising the step of testing a biological sample from a patient to determine the presence of a marker protein (P210) which is characterized as a c-abl protein having tyrosine kinase activity and a molecular weight of approximately 210,000. Antisera which are specific for the P210 protein are disclosed which can be used to precipitate the P210 protein to allow identification by gel electrophoresis or other technique.

7 Claims, No Drawings

METHOD AND COMPOSITION FOR DETECTION OF HUMAN CHRONIC MYELOGENOUS LEUKEMIA

This invention was made with Government support under Grant No. CA 27507 awarded by the National Institutes of Health. The Government has certain rights in this invention.

BACKGROUND OF THE INVENTION

The present invention relates generally to methods and reagents used in the detection of cancer. More particularly, the present invention relates to a new diagnostic approach for the detection of chronic myelogenous leukemia.

Leukemia is a malignant disease of the blood-forming organs which involves the distorted proliferation and development of leukocytes and their precursors in bone marrow and blood. There are different types of leukemia which are classified according to two basic considerations: (1) the duration and character of the disease—acute or chronic and (2) the type of cell involved—myeloid (myelogenous) or lymphoid (lymphogenous).

In general, the different types of leukemia are restricted to different age groups. For example, acute lymphoid leukemia generally occurs in young children while acute myelogenous leukemia is found principally in young adults. The chronic forms of leukemia are found principally in adults.

Although there is no known treatment that can permanently control or cure leukemia, there are a wide variety of therapies available which have been successful at prolonging the life of many patients. The treatments range from transfusion and replacement of blood cells to the use of radiation therapy, corticosteroid therapy, chemotherapy using antineoplastic agents, antibiotics and immunotherapy. Different therapies are utilized depending upon the type of leukemia being treated. For example, often no treatment is necessary for chronic lymphoid leukemia, except for occasional radiation therapy. On the other hand, acute leukemia requires immediate treatment utilizing the full range of therapeutic measures available.

Present techniques for diagnosing leukemia are time consuming and do not provide a completely unambiguous determination of the type of leukemia present. It would be desirable to provide a quick, accurate and positive diagnosis procedure which is capable of detecting one or more of the various types of leukemia.

SUMMARY OF THE INVENTION

In accordance with the present invention, a method is provided for detecting chronic myelogenous leukemia which is simple, accurate and quick. The present invention is based upon the discovery that the c-abl protein normally found in humans is present in an altered state in individuals having chronic myelogenous leukemia. The altered c-abl protein exhibits tyrosine kinase activity which is not present in normal human c-abl protein and further has a molecular weight of approximately 210,000 which is much higher than the normal c-abl molecular weight of 150,000.

The method for detecting chronic myelogenous leukemia in humans in accordance with the present invention involves testing a biological sample from the patient to determine whether or not the above referenced marker protein is present. Any number of immunoprecipitation/gel electrophoresis methods along with radioimmunoassay, immunofluorescence, immunoperoxidase and other assays may be utilized in determining the presence of the marker protein.

As a particular feature of the present invention, determining the presence of the marker protein involves immunoprecipitating the marker protein from the sample with an antibody which is reactive with the marker protein to form an immunoprecipitate. The immunoprecipitate is then identified by conventional gel/electrophoresis or other suitable separation/detection techniques.

As another feature of the present invention, the antibodies used in immunoprecipitating the marker protein are produced by preparing a peptide having an amino acid sequence corresponding to the amino acid sequence of a selected portion of v-abl protein. V-abl protein is a known transforming protein of Abelson murine leukemia virus. The v-abl protein is known to have tyrosene-specific kinase activity which is involved in the viruses ability to transform cells. The c-abl protein is the normal cellular homolog of v-abl.

The synthetic peptide corresponding to the selected amino acid sequence of v-abl protein is then coupled to a suitable non-toxic animal compatible protein carrier and administered to an animal to raise antibodies which are capable of immunoprecipitating the newly discovered protein marker.

As another feature of the present invention, antibodies for use in immunoprecipitating and identifying the protein marker can be prepared by producing fusion proteins from bacteria containing plasmids which express the fusion protein with the fusion protein also being administered to an animal to raise antibodies which are effective in immunoprecipitating the marker protein.

As another feature of the present invention, a diagnostic reagent is provided which includes antibodies capable of immunoprecipitating the marker protein from a biological sample removed from the patient.

The diagnostic technique in accordance with the present invention is an improvement over prior diagnosis techniques which involve a combination of various time consuming procedures which provide results which can sometimes be ambiguous. The present inventions involves an accurate and unambiguous diagnosis of chronic myelogenous leukemia based on the detection of a single, specific protein marker.

The above discussed and many other features and attendant advantages of the present invention will become apparent as the invention becomes better understood by reference to the following detailed description.

DETAILED DESCRIPTION OF THE INVENTION

The present invention basically involves a method for detecting chronic myelogenous leukemia (CML) in humans by determining the presence of a specific protein marker in the bone marrow, blood tissue or other suitable sample taken from a patient.

The specific protein marker is an altered form of the c-abl protein. The c-abl protein (MW 150,000) is the normal cellular homolog of the transforming protein v-abl of the Abelson murine leukemia virus (A-MulV).

The v-abl protein is known to be a tyrosine-specific protein kinase. Several lines of evidence have shown that the tyrosine-specific kinase activity of the v-abl protein, encoded by c-abl derived sequences, mediates the ability of A-MulV to transform (Witte, O. N., Dasgupta, A. and Baltimore, D. (1980). Abelson murine leukemia virus protein is phosphorylated in vitro to form phosphotyrosine. Nature 283, 826–831; Witte, O. N., Goff, S. P., Rosenberg, N. and Baltimore, D. (1980). A transformation defective mutant of Abelson murine leukemia virus lacks protein kinase activity. Proc. Natl. Acad. Sci. USA 77, 4993–4997; Reynolds, R. K., van de Ven, W. J. M. and Stephanson, J. R. (1980). Abelson murine leukemia virus transformation defective mutants with impaired P120 associated protein kinease activity. J. Virol. 36, 374–386; Prywes, R., Foulkes, J. G., Rosenberg, N. and Baltimore, D. (1983) Sequences of the A-MuLV protein needed for fibroblast and lymphoid cell transformation. Cell 34, 569–579; and Rosenberg, N. E., Clark, D. R. and Witte, O. N. (1980) Abelson murine leukemia virus mutants deficient in kinase activity and lymphoid cell transformation. J. Virol. 36, 766–774.)

Although the v-abl and c-abl proteins are closely related, they differ in that the c-abl protein is not detectably phosphorylated on tyrosine in vivo or in vitro (Ponticelli, A. S., Whitlock, C. A., Rosenberg, N. and Witte, O. N. (1982). In vivo tyrosine phosphorylations of the Abelson virus transforming protein are absent in its normal cell homolog. Cell 29, 953–960).

In accordance with the present invention, an altered, higher molecular weight (MW 210,000) c-abl protein (P210) was found in cells from a chronic myelogenous leukemia patient. The altered P210 c-abl protein was found to be phosphorylated on tyrosine in vivo and was also phosphorylated on tyrosine during in vitro kinase reactions, similar to the v-abl protein. This P210 protein is useful as a marker to identify cells which are present in CML patients.

The particular test used to identify the P210 protein is not particularly critical. Any of the well known techniques for isolating and identifying proteins may be used. Suitable techniques include immunoprecipitation/gel electrophoresis, "Western" blotting, radioimmunoassay, immunofluorescence, immunoperoxidase, enzyme linked immunosorbient assay (ELISA) and measurement of tyrosine kinase activity levels on cell extracts or in situ.

Although numerous different protein separation and detection techniques are possible, it is preferred to use techniques involving immunoprecipitation of the protein marker coupled with separation and identification by gel electrophoresis. Examples of the isolation, detection and characterization of the P210 protein marker and preparation of suitable antibody immunoprecipitation reagents is as follows:

We examined c-abl protein expression in the human K562 leukemia cell line. The K562 cell line was isolated from a patient with chronic myelogenous leukemia (CML) in blast crisis (Lozzio, C. B. and Lozzio, B. B. (1975) Human chronic myelogenous leukemia cell line with positive Philadelphia chromosome. Blood 45, 321–334.) K562 cells have a 9:22 chromosomal translocation involving the c-abl gene (Collins, S. J. and Groudine, M. T. (1983). Rearrangement and amplification of c-abl sequences in the human chronic myelogenous leukemia cell line K562. Proc. Natl. Acad. Sci. USA 80, 4813–4817.) which is a common characteristic of CML patients (Rowley, J. D. (1973) A new consistent chromosomal abnormality in chronic myelogenous leukemia identified by Quniacrine fluorescence and Giemsa staining. Nature 243, 290–291; and Fialkow, P. J., Martin, P. J., Najfeld, V., Penfold, G. K., Jacobson, R. J. and Hansen, J. A. (1981) Evidence for a multistep pathogenesis of chronic myelogenous leukemia. Blood 58, 158–163.) Recent evidence indicates that the translocation breakpoint occurs near the 5' end of the c-abl gene in K562 cells as well as in cells from CML patients that have the characteristic 9:22 translocation (Groffen, J., Stephenson, J. R., Heisterkamp, deKlein, A., Bartram, C. R. and Grosfeld, G. (1984) Philadelphia chromosomal breakpoints are clustered within a limited region, bcr, on chromosome 22. Cell 36, 93–99; Heisterkamp, N., Stephenson, J. R., Groffen J., Hansen, P. F., deKlein, A., Bartram, C. R. and Grosfeld, G. (1983) Localization of the c-abl oncogene adjacent to a translocation point in chronic myelocytic leukemia. Nature 306, 239–242.) In addition, the c-abl gene is amplified 4 to 8 fold in K562 cells (Collins and Groudine, 1983, supra). Using abl-specific site directed antisera for immunoprecipitation analysis, we detected the altered, higher molecular weight P210 c-abl protein in the K562 cells. The abl specific antisera were prepared as described in the paper entitled "Only Site-Directed Antibodies Reactive With the Highly Conserved Src-Homologous Region of the v-abl Protein Neutralize Kinase Activity," J. B. Konopka, R. L. Davis, S. M. Watanabe, A. S. Ponticelli, L. SchiffMaker, N. Rosenberg and O. N. Witte, Journal of Virology, July 1984, p. 223–232, the contents of which is hereby incorporated by reference.

The antisera were prepared by two different procedures. The first involved selecting amino acid sequences from different regions of the v-abl protein and preparing synthetic peptides corresponding to the selected amino acid sequences. The peptides were then conjugated to a suitable carrier such as Keyhole limpet hemocyanin (KLH) and then administered to rabbits to raise the desired antisera. Plasma albumin is also a suitable carrier. Five different antisera were prepared as follows:

T-Butyloxycarbonyl (Boc)-protected amino acids were purchased from Vega Biochemicals, except for lysine, which was purchased from Bachem Fine Chemicals. Inc. Boc-[$^{14}$C]glycine and Boc-[$^{14}$C]alanine were prepared by diluting 0.25 mCi of free [$^{14}$C]glycine or [$^{14}$C]alanine (Amersham) into the appropriate non-radioactive amino acid, followed by reaction with di-t-butyl-dicarbonate [(Boc2)]0 (Moruder, L. A. Hallet, E. Wunsch, O. Keller and G. Wersin. 1976. Di-tert.-butyl-dicarbonat-ein vorteilhaftes reagenz zur Einfuhrung der tert.-Butyloxycarbonyl-schutzgruppe. Hoppe-Seyler's Z. Physiol. Chem. 357:1651–1654). N,N'-Dicyclohexyl-carbodiimide, 1-hydroxybenzotriazole, and 99% distilled trifluoroacetic acid were obtained from Aldrich Chemical Co.; hydrogen bromide gas was purchased in a Lecture bottle from Matheson. Keyhole limpet hemocyanin (KLH) was obtained from Calbiochem-Behring. Complete and incomplete Freund adjuvant were purchased from GIBCO.

Peptides were synthesized by the solid-phase method of Merrifield, using N,N'-dicyclohexylcarbodiimide/1-hydroxybenzotriazole activation (Stewart, J. M., and J. D. Young. 1969. Solid phase peptide synthesis. Freeman, Cooper & Co., San Francisco.) The amino acid sequences of the 5 chemically synthesized peptides are as follows: TyrLysGluArgGlyProProAspGlySer-Leu (peptide 1), TyrLysGlyAlaSerGluAspAspSerArg-GluLeu (peptide 2), TyrGluGluAlaAlaGluGluGly-PheLysAspThrGluSerSerProGlySerSerProProSerLeu (peptide 3), TyrSerAspGluValGluLysGluLeuGlyLys (peptide 4), and TyrGlyGluValTyrGluGlyValPheLysLys (peptide 5).

A $^{14}C$-labeled glycine or alanine residue was incorporated into each peptide as a radiolabeled tracer for later processing. Peptides 1, 2, 3, and 4 have an artificial addition of tyrosine at their amino termini to allow for possible iodination in radioimmunoassay, as well as for possible alternative coupling to carrier protein through the tyrosine hydroxyl group. Peptide 2 has an artificial addition of lysine penultimate to the amino-terminal tyrosine. Peptide 5 has a substitution of phenylalanine for tryptophan in the Abelson sequence, since the indole ring of tryptophan is highly sensitive to the conditions used for cleaving the completed peptide from the support matrix. Thus, the closest related amino acid, phenylalanine, replaced the tryptophan to make peptide 5 amenable to our established synthesis procedure.

Peptides were cleaved from their support resins by a 90-min incubation in 99% trifluoroacetic acid in the presence of bubbling hydrogen bromide gas. To prevent the formation of bromotyrosine, the hydrogen bromide gas was scrubbed in the presence of a $5 \times$ molar excess to peptide of anisole as a scavenger. After cleavage, the peptides were repeatedly washed with methanol and dried by evaporation. Several ether extractions were performed to remove the anisole and other organic contaminants. One cycle of lyophilization was performed to yield a crude crystalline product. The peptides were purified by subjecting them to gel filtration chromatography, using either Bio-Rad P2 or P4 in 50 mM formic acid, pH 2.5. Column fractions were analyzed by optical density, at 280 nm for molecular weight standards and by $^{14}C$ scintillation copeptides. Fractions overlapping with the single $^{14}C$ activity peak observed for each peptide were pooled and lyophilized to a white, fluffy crystalline product.

The peptides were then coupled to a carrier as follows. Crystalline peptide was dissolved in 0.1M $NaH_2PO_4$-$Na_2HPO_4$ (pH 7.2)-0.15M NaCl at room temperature. KLH in 0.15M NaCl was added such that the peptide was at a $75 \times$ molar excess per 100,000 molecular-weight of KLH. The reaction was performed by slow addition of 20 mM glutaraldehyde to a final concentration of 6.7 mM. After a 30-min incubation with stirring, the conjugate was dialyzed extensively against phosphate-buffered saline at 4° C. Peptide KLH conjugate was stored at 4° C. Efficiency of coupling was determined by measuring $^{14}C$ activity in the reaction mixture before the addition of glutaraldehyde and after dialysis. On average, the coupling was 50% efficient.

Bleedings and immunizations. The peptide KLH conjugates were emulsified in an equal volume of complete Freund adjuvant. For each peptide-KLH conjugate, two adult, female New Zealand White rabbits were prebled for normal sera on day 0 and injected subcutaneously at four to six sites in their posterior, axial lymph node regions, with 1 mg of conjugate (ca. 300 micrograms of peptide). The rabbits were boosted at the same dosage of conjugate emulsified in incomplete Freund adjuvant every 2 to 3 weeks. Intraperitoneal injections were interspersed with the regular subcutaneous injections in the schedule. The sera containing the desired v-abl and P210 specific antibodies was then harvested from the rabbits according to conventional procedures.

The second antibody preparation procedure involved construction of plasmids expressing the trp-abl fusion protein and incorporating the plasmids into E. coli. The procedure for constructing the plasmids and induction of trpE-abl fusion proteins in E. coli is as follows.

The Abelson sequences expressed in all of the fusion proteins were subcloned from pAB160 (Latt, S. A., S. P. Goff, C. J. Tabin, M. Paskind, J. Y. J. Wang and D. Baltimore. (1983). Cloning and analysis of reverse transcript P160 genomes and Abelson murine leukemia virus. J. Virol. 45:1195–1199). The 2.2-kilobase (kb) Bg/II fragment subcloned to construct pEX-1 was purified by low melting point agarose gels (Bethesda Research Laboratories, Inc., Rockville, Md.) and then extracted with hexadecyltrimethylammonium bromide. Langridge, J. P. and Berquist, P. L. 1980. Extraction of nucleic acids from agarose gels. Anal. Biochem. 103:246–271. The fragment was ligated to pKRS101. Spindler, K. R., Rosser, D. E., and Berk, A. J. 1984. Analysis of adenovirus transforming proteins from early regions 1A and 1B with antisera to inducible fusion antigens produced in Escherichia coli. J. Virol. 49:132–141. Cell 32:891–901) treated with Bg/II(P-L Biochemicals, Inc., Milwaukee, Wis.) and calf intestinal phosphatase (Boehringer Mannheim Biochemicals, Indianapolis, Inc.). Ligations were transformed into $CaCl_2$-shocked (Mandel, M. and A. Higa. 1970 Calcium dependent bacteriophage DNA infection. J. Mol. Biol. 53:159–162) Escherichia coli HB101. Ampicillin-resistant colonies were screened by minilysates for the presence of the 2.2-kb Bg/II fragment and for the correct orientation of that fragment. Minilysates from the appropriate colonies were then used to transform $CaCl_2$-shocked E. coli C600. These cells were induced (see below) for expression of pEX-1. pEX-2 was derived from pEX-1 by digesting cesium chloride-ethidium bromide-purified pEX-1 plasmid with SstI (P-L Biochemicals). Ligations were then carried out under dilute conditions (10 micrograms/ml) and transformed into $CaCl_2$-shocked E. coli C600. Colonies were screened by minilysate for deletion of a 0.7-kb SstI fragment.

The abl sequence expressed in pEX-4 was subcloned by digesting pAB160 with PstI and HindIII (P-L Biochemicals). Fragments were ligated to pUC12 (Viera, J. and J. Messing. (1982). The pUC plasmids, an M13mp7-derived system for insertion mutagenesis and sequencing with synthetic universal primers. Gene 19:259–268) which had been treated with PstI and calf intestinal phosphatase. Ligation reactions were transformed into $CaCl_2$-shocked E. coli JM83 and grown in the presence of the chromogenic substrate 5-bromo-4-chloro-3-indoly-1-beta-galactoside (X-gal) (Sigma). White colonies were screened by minilysates for plasmids containing a 0.9-kb PstI fragment in the correct orientation. An appropriate colony was picked, and supercoiled DNA was purified by cesium chloride-ethidium bromide centrifugation. This DNA was then digested with SstI, which cuts in the polylinker region of pUC12 and in the abl sequences. The restricted DNA was religated under dilute conditions (1 microgram/ml) and transformed into $CaCl_2$-shocked E. coli HB101. Colonies were screened for loss of the SstI fragment. An appropriate colony was selected, and plasmid DNA was purified by cesium chloride-ethidium bromide centrifugation. Plasmid DNA was restricted by HindIII (International Biotechnologies, Inc.) and EcoRI. The EcoRI-HindIII fragment was purified through an agarose gel, hexadecyltrimethylammonium bromide extracted, and ligated to pJH14, which had been digested by EcoRI and HindIII. Ligations were transformed into $CaCl_2$-shocked E. coli HB101. Colonies were screened by minilysates for the presence of the insert. Minilysate DNA from appropriate colonies was then used to transform E. coli C600. Ampicillin-resistant colonies were rescreened for presence of pEX-4 and then induced (see below).

The construction of pEX-5 involved digestion of pAB160 with HindIII and SalI (P-L Biochemicals). The 1.1-kb HindIII-SaII abl fragment was purified in low melting point agarose and hexadecyltrimethylammonium bromide extracted. pJH12 was HindIII and SalI digested and then ligated to the gel-purified Abelson insert. Ligation reactions were transformed into $CaCl_2$-shocked E. coli HB101. The resulting colonies were screened for the insert by minilysates. Minilysates from selected colonies were used to transform $CaCl_2$-shocked E. coli C600. Ampicillin-resistant colonies were screened for production of pEX-4 by minilysates and then induced.

E coli C600 cells carrying the trpE-abl fusion plasmids were induced as previously described (Kleid, D. G., D. Yansura, B. Small, D. Dowbenko, D. M. Moore, M. J. Grubman, P. D. McKercher, D. O. Morgan, B. H. Robertson and H. L. Bachrach. 1981 Cloned viral protein vaccine for foot-and-mouth disease: Responses in cattle and swine. Science 214:1125-1128; Snyder, M. A., J. M. Bishop, W. W. Colby and A. D. Levinson. 1983 Phosphorylation of tyrosine 416 is not required for the transforming properties and kinase activity of pp60v-$src$. Cell 32:891-901).

Cultures were inoculated from frozen stocks (−70° C.) and grown overnight at 37° C. in M9 ((Maniatis, T., F. Fritsch and J. Sambrook. 1982 *Molecular Cloning.* Cold Spring Harbor Laboratory, Cold Spring Harbor, N.Y.) plus 1% Casamino Acids and 100 micrograms of ampicillin and 20 micrograms of tryptophan per ml. Overnight cultures were diluted 1:100 into fresh M9 with 1% Casamino Acids plus 100 micrograms of ampicillin per ml and grown to an optical density at 600 nm of 0.2. Expression of the trpE-abl fusion proteins was then induced by adding 100 microliters of a 20-micrograms/ml solution of 3-beta-indoleacrylic acid (Sigma) in ethanol to 100 ml of culture. Growth was continued to late log phase (8 h), and then the cells were harvested by centrifugation and stored at −20° C.

Induction of the expected fusion protein was monitored by lysing induced and uninduced cells directly in 2×concentrated SDS gel sample buffer and then analyzing the expressed proteins by SDS-polyacrylamide gel electrophoresis, followed by staining with Coomassie brilliant blue. As a control, induced and uninduced cells carrying the parental trpE expression vector were also analyzed.

Fusion proteins were partially purified from induced cell pellets as described previously. Frozen cell pellets from 100 ml of culture were suspended in 10 ml of TEN (50 mM Tris-hydrochloride [pH 7.5], 0.05 mM EDTA, 0.3M NaCl) and incubated for 15 min on ice with lysozyme (1 mg/ml) and then 220 microliters of a 10% Nonidet P-40 solution. After a 10-min incubation, 15 ml of 1.5 ml of NaCl, 12 mM $MgCl_2$, and 100 microliters of 2 mg of DNase I (Sigma) per ml was added. The DNase I treatment continued for 1 h on ice with shaking. The fusion proteins were recovered as insoluble protein after centrifugation for 15 min at 8,000×g. The insoluble protein pellets were washed twice with 4 ml of TEN. For gel electrophoresis, the insoluble protein pellets were solubilized by boiling in 2×SDS gel sample buffer for 20 min.

pEX-4 could not be purified by this procedure, as it was degraded. Instead, conditions for the expression of pEX-4 were optimized after a time course of induction, and a total cell lysate of induced pEX-4 cells was prepared by boiling in 2X SDS gel sample buffer for 20 min.

Immunizations with trpE-abl fusion proteins. Fusion proteins were further purified by preparative SDS gel electrophoresis on 1.5 or 3.0-mm-thick 8% polyacrylamide gels as described previously (Kleid et al. and Snyder et al., supra). The side lanes of the gel were stained with Coomassie brilliant blue to identify the position of the fusion protein in the gel. The area of the gel containing the fusion protein was excised and homogenized in complete Freund adjuvant (GIBCO) by serial passage through 18-, 20-, and 22-gauge syringe needles. New Zealand white female rabbits (Mission Laboratories) weighing 2 kg were immunized with 500 micrograms of protein each. The rabbits were then boosted with 250 micrograms of fusion protein every two weeks, and serum was collected 7 days after each boost.

Five of the antisera prepared as set forth above were used to immunoprecipitate proteins from various cell lines. The different regions of the v-abl protein recognized by the five antisera used in those examples are diagrammed and described as follows:

Sera harvested from rabbits immunized with the previously described chemically synthesized peptides 3 and 5 are designated pep3 and pep5 respectively. Sera harvested from rabbits immunized with regions of the v-abl protein expressed as trpE-abl fusion proteins in bacteria are designated αpEX-2, αpEX-4, and αpEX-5. The regions of the v-abl protein against which these antisera are directed are indicated on the P160 molecule shown below. All of these antisera were previously shown to have the expected specificity using deletion mutants of A-MuLV (Konopka et al., 1984, supra).

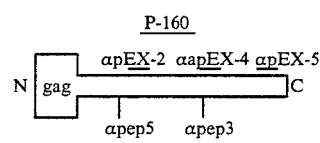

For immunoprecipitation analysis, cells were metabolically labeled with $^{32}P$-orthophosphate, detergent extracted, immunoprecipitated with anti-v-abl sera, and then analyzed by polyacrylamide gel electrophoresis and autoradiography. All five of the v-abl antisera immunoprecipitated the P160 v-abl protein. The specificity of the antisera for c-abl immunoprecipitation was analyzed using SCRF60A, a murine thymoma cell line (Lerner, R. A., Jensen, F., Kennel, S. J., Dixon, F. J., Des-Roches, F. and Francke, U. (1972). Karyotypic, virologic, and immunological analyses of two continuous lymphocyte cell lines established from New Zealand black mice: possible relationship of chromosomal mosaicism to autoimmunity. Proc. Natl. Acad. Sci. USA 69, 2965-2969.) previously reported to be a good source of c-abl (Ponticelli, et al. (1982, supra). It was found that all five of the v-abl antisera examined precipitated a 150,000 MW phosphoprotein-P-150. This was in agreement with previous studies using anti-A-MuLV induced tumor sera (Witte, O. N., Rosenberg, N. and Baltimore, D. (1979). A normal cell protein cross-reactive to the major Abelson murine leukemia virus gene product. Nature 281,: 396–398.) Examination of the control pre-immune sera and comparison with the results for the immune sera indicates that only the P150 c-abl protein is specifically immunoprecipitated from SCRF60A cells.

c-abl protein expression was also examined in the transformed human hematopoietic tumor cell lines K562 and HL-60 (Collins, S. J., Gallo, R. C. and Gallagher, R. E. (1977). Continuous growth and differentiation of human myeloid leukemia cells in suspension culture. Nature 270, 347–349). DNA blot hybridization analysis using a v-abl probe has confirmed that the K562 cells used in our examples have an altered c-abl gene structure including a 4 to 8-fold amplification relative to normal human controls as previously reported (Collins, S. J. and Groudine, M. T. (1983). Rearrangement and amplification of c-abl sequences in the human chronic myelogenous leukemia cell line K562. Proc. Natl. Acad. Sci. USA 80, 4813–4817).

Immunoprecipitation of K562 and control human cell lines including HL-60 with the above 5 anti sera resulted in precipitation of an approximately 145,000 MW protein (P145). The human P145 c-abl protein is also a phosphoprotein but has a slightly lower apparent molecular weight on SDS-polyacrylamide gels than the 150,000 MW murine c-abl protein protein P150. Although all five of the v-abl antisera precipitated the P145 human c-abl, two of the antisera, anti-peptide 3 and anti-pEX-4, cross-react weakly with human c-abl. Both of these antisera are directed against a region of the v-abl protein deleted in the P120 strain of A-MuLV without grossly altering transforming or kinase activity (Goff, S. P., Witte, O. N., Gilboa, E., Rosenberg, N. and Baltimore, D. (1981). Genome structure of Abelson murine leukemia virus variants: proviruses in fibroblasts and lymphoid cells. J. Virol. 38, 460–468.) The apparent lack of conservation of sequence in this region suggests that it may not be a functionally important region of the v-abl protein.

Two unique higher apparent molecular weight species were precipitated by all five of the v-abl antisera from K562 cells. The two higher molecular weight species were estimated to be approximately 190,000 MW (P190) and 210,000 MW (P210) relative to stained molecular weight standards on the gel. P210 and P190 were detected in K562 cells but not in control human cell lines HL-60, CCRF-CEM, or 293, or in any of the murine cells examined. These proteins appear to be abl-related as the amount of P210 and P190 precipitated with each antisera correlates with the amount of P145 precipitated in each lane. Furthermore, precipitation of P210, P190, and P145 by the antipeptide sera can be blocked by addition of the appropriate competing peptide to the immunoprecipitation reaction. The amount of P190 detected varied relative to P145 and P210 in different preparations suggesting that P190 may represent a proteolytic fragment of P210. The increase in apparent molecular weight observed for P210 could be the result of post-translational modifications of P145, or insertion of additional coding sequences into the c-abl gene.

The relatedness of the three c-abl species detected in K562 cells was further established by two-dimensional phosphopeptide mapping. Each form of c-abl was immunoprecipitated from cells metabolically labeled in vivo with $^{32}$p-orthophosphate, run on preparative SDS-polyacrylamide gels, extracted, performic acid oxidized, and then digested completely with trypsin. Phosphopeptides were analyzed by thin layer electrophoresis in the first dimension followed by thin layer chromatography in the second dimension.

Analysis in the first dimension was carried out by electrophoresis for 1 hr at 400 V in 1% ammonium carbonate pH 8.9 on thin layer cellulose plates. Ascending chromatography in the second dimension was performed in n-butanol-pyridine-acetic acid $H_2O$ (15:10:3:12). Plates were autoradiographed with an intensifying screen for 1 day or 7 days. The P145 human c-abl proteins from control human and K562 cell lines resulted in phosphopeptide maps that are indistinguishable within the limits of this analysis. When the P190 and P210 c-abl proteins were analyzed it was found that the phosphopeptide maps generated were industinguishable from the phosphopeptide map for P145 c-abl. Therefore, the serologically identified normal P145 normal c-abl is also structurally related to P190 and P210 c-abl proteins. As will be described below P210 and P190 differ from normal P145 c-abl in that they are phosphorylated on tyrosine in vivo. However, we could not detect a corresponding new phosphopeptide in our analysis.

To assay for in vitro kinase activity, cell extracts were immunoprecipitated and then incubated with [$v^{32}$P]ATP under conditions which allow v-abl autophosphorylation (Witte, O. N., Desgupta, A and Baltimore, D. (1980). Abelson murine leukemia virus protein is phosphorylated in vitro to form phosphotyrosine. Nature 283, 826–831.) The procedure was as follows.

P160 v-abl transformed M1-44 cells, murine thymoma cell line SCRF60A, control human cell line CCRF-CEM and K562 cells were metabolically labeled with [$^{35}$S] methionine, extracted, and immunoprecipitated with normal rabbit serum or αpEX-5. For in vitro phosphorylation assays, cell extracts were immunoprecipitated with normal rabbit serum, αpEX-2, αpEX-4, or αpEX-5. Immunoprecipitates were washed and then incubated in 20 mM PIPES (piperazinediethanesulfonate) pH 7.0 containing 10 mM $MnCl_2$ and 5 Ci [$v^{32}$P]ATP for 5' at 30° C. Samples were washed and then analyzed by SDS-polyacrylamide gel electrophoresis and autoradiography for 1 day. [$^{35}$S]-methionine samples were detected by fluorography for 3 days.

The reaction products were then analyzed by SDS-polyacrylamide gel electrophoresis and autoradiography. Autophosphorylation of the P160 v-abl protein was detected, but in vitro phosphorylation of P150 c-abl from a murine cell line or P145 c-abl from a control human cell line was not observed. However, the phosphorylation of the high molecular weight species was observed in K562 immunoprecipitates prepared with v-abl antisera. This phosphorylated species was not observed in the normal serum control. Comparison with an immunoprecipitate prepared from K562 cells metabolically labeled with [$^{35}$S]-methionine demonstrates that the P210 c-abl protein becomes phosphorylated in vitro. Phosphorylation of the P145 c-abl in K562 cells was not detected. P210 precipitated with αpEX-4 sera was generally phosphorylated to a lesser extent relative to P210 precipitated with αpEX-2 and αpEX-5 sera.

The variable extent of P210 in vitro phosphorylation may be due to the weak cross-reactivity of the αpEX-4 sera with human c-abl proteins. P210 c-abl was phosphorylated to a similar extent as P160 v-abl prepared from a 30-fold dilution of P160 transformed cell extract. This relative difference in extent of in vitro phosphorylation corresponds to the relative amount of P160 and P210 detected in vivo following a two-hour pulse labeling with 32P-orthophosphate. The in vitro phosphorylation reactions for P210 c-abl and P160 v-abl share several common features. Both reactions prefer $Mn^{++}$ to $Mg^{++}$ as a source of cation in the reaction mix and both in vitro reactions are complete in less than 5 minutes at 30° C. In addition, no phosphorylation of the immunoglobulin heavy chains was observed as a result of the P210 c-abl or P160 v-abl in vitro phosphorylation reactions as is commonly observed for the related tyrosine kinase pp60$^{src}$ (Erikson, E. and Purchio, A. F. (1979). Evidence that the avian sarcoma virus transforming gene product is a cyclic AMP-independent protein kinase. Proc. Natl. Acad. Sci. USA 76, 6260–6264). When the sites of in vitro phosphorylation were compared by two-dimensional phosphopeptide mapping, it was found that P210 was phosphorylated at one major site which was distinct from the two major sites observed for P160 v-abl.

The phosphoamino acid composition of P160 v-abl and P210 c-abl phosphorylated in vitro with [$v^{32}P$]ATP was determined by partial acid hydrolysis of gel-extracted proteins and subsequent analysis by thin layer electrophoresis. The results demonstrate that both P210 c-abl and P160 v-abl are phosphorylated on tyrosine in vitro. The phosphoamino acid analysis was carried out as follows:

P160 v-abl and P210 c-abl were phosphorylated in vitro using [$v^{32}P$]ATP and electrophoresed on an 8% SDS-polyacrylamide gel. The phosphorylated proteins were eluted from the gel and hydrolysed for 2 hrs at 100° C. in 6N HCl. Hydrolysates were lyophilized, resuspended in a mixture of phosphoamino acid standards, and then approximately 2000 CPM of each sample was analyzed by electrophoresis on a thin layer cellulose plate. Electrophoresis was toward the anode at the top in pyridine-acetic acid-H$_2$O (5:50:945) for 3 hrs at 400 V. Phosphoamino acid composition of in vitro phosphorylated P160 and P210 was visualized by autoradiography for 3 days. Non-radioactively labeled phosphoamino acid standards were detected by ninhydrin straining.

In addition, a small amount of phosphoserine was detected for P210 c-abl but not for P160 v-abl. Possibly this represents a low level of contaminating kinase activity seen for P210 but not for P160 v-abl in vitro phosphorylation reactions which incorporate 25- to 50-fold more $^{32}P$.

It has been shown that P150 murine c-abl is not detectably phosphorylated on tyrosine in vivo as is the P160 v-abl protein (Ponticelli, et al., supra). To further compare the different forms of human c-abl, we examined their phosphoamino acid composition following metabolic labeling with $^{32}P$-orthophosphate.

P160 v-abl, P150 murine c-abl, P145 human c-abl from a control cell line CCFR-CEM, and P145, P190 and P210 human c-abl proteins from K562 cells were metabolically labeled in vivo with $^{32}P$ orthophosphate. The proteins were isolated and phosphoamino acid analysis was performed as previously described for the phosphoamino acid analysis except that approximately 750 CPM of each sample was analyzed. Phosphoamino acids were detected by autoradiography for 10 days with an intensifying screen. Non-radioactively labeled phosphoamino acid standards were detected by ninhydrin staining (not shown).

The results of this analysis indicate that the P210 and P190 human c-abl species from K562 cells were phosphorylated on tyrosine in vivo. In addition, our analysis indicates that the P145 human c-abl protein from K562 cells was also phosphorylated on tyrosine, but to a lesser extent than the P210 c-abl protein. However, the P145 c-abl protein from a control human cell line and the P150 murine c-abl protein were not detectably phosphorylated on tyrosine. In similar experiments we have not detected in vivo phosphorylation on tyrosine of the P150 murine c-abl protein isolated from A-MuLV transformed cells. The correlation of the in vitro and in vivo phosphorylation on tyrosine of the P210 c-abl protein indicates that P210 is a tyrosine-specific portein kinase capable of autophosphorylating in vitro and catalyzing the formation of phosphotyrosine in vivo similar to the v-abl protein.

The structural differences between P145 and P210 c-abl may be important for unmasking associated tyrosine kinase activity. In order to localize the altered sequences, in vitro phosphorylated P210 was partially digested with S. aureus V-8 protease and then immunoprecipitated with antisera against the amino terminal (αpEX-2) and carboxyl-terminal (αpEX-5) regions of the v-abl protein.

The in vitro phosphorylated P210 and P160 were prepared as previously described using [$v^{32}P$]ATP. The proteins were eluted from the immune complex with 100 microliters of SDS gel sample buffer per 20 microliters of pEX-5 sera used. The samples were then incubated with an equal volume of 0.3 microgram/ml S. aureus V-8 protease for 30 min at 37° C. The digests were terminated by incubation at 80° for 5 min followed by dilution into immunoprecipitation buffer (PLB). The partially digested proteins were then immunoprecipitated with antisera directed against the amino terminal region (αpEX-2) and the carboxy-terminal region (αpEX-5) of the v-abl protein. Samples were analyzed by electrophoresis on an 8% SDS polyacrylamide gel and autoradiography with an intensifying screen for 1 day.

An approximately 185,000 MW fragment (F185) of the P210 protein was generated which precipitated with the amino terminal directed antisera (αpEX-2) but not with antisera against the carboxyl region of the v-abl protein (αpEX-5). The generation of F185, which has lost sequence cross-reacting with the v-abl carboxyl terminus, indicates that P210 c-abl and P160 v-abl have similar carboxyl terminal regions. This suggests that the altered sequences must be located internally or at the amino terminus of P210. The lack of other detectable preteolytic fragments prevents further localization of the altered sequences by this analysis. Similar experiments using in vitro phosphorylated P160 v-abl demonstrate that there were proteolytic fragments which immunoprecipitated with the amino terminal directed antisera (αpEX-2) but not with antisera directed against the carboxyl terminus of the v-abl protein (αpEX-5). This is in agreement with previous results localizing the in vitro phosphorylation sites to the amino terminal region of the v-abl protein (Witte, O. N., Ponticelli, A., Gifford, A., Baltimore, D., Rosenberg, N. and Elder, J. (1981). Phosphorylation of the Abelson murine leukemia virus transforming protein. J. Virol. 39, 970–878.

The c-abl gene was identified by DNA hybridization analysis using a v-abl probe (Goff, S. P., Gilboa, E., Witte, O. N. and Baltimore, D. (1980). Structure of the Abelson murine leukemia virus genome and the homologous cellular gene: studies with cloned viral DNA. Cell 22, 777–785.) and has been subsequently cloned from the murine and human genomes (Wang, J. Y. J., Ledley, F., Goff, S., Lee, R., Groner, Y. and Baltimore, D. (1984); Heisterkamp, et al., supra). Analysis of the cloned murine c-abl gene indicates that it is spread over approximately 40 kb and is composed of at least 10 exons. Partial DNA sequence analysis indicates that v-abl and murine c-abl probably have a common carboxyl terminus, but that there are additional amino terminal sequences in c-abl that are not present in the v-abl protein (Wang et al., 1984, supra). Two c-abl RNA species have been detected in several murine and human cell lines and tissues (Wang, J. Y. J. and Baltimore, D. (1983). Cellular RNA homologous to the Abelson murine leukemia virus transforming gene: Expression and relationship to the viral sequence. Mol. Cell. Biol. 3, 773–779; and Muller, R., Slamon, D. J., Tremblay, J. M., Cline, M. J. and Verma, I. M. (1982). Differential expression of cellular oncogenes during pre- and postnatal development of the mouse. Nature 229, 640–644). However, using abl-specific antisera, and in previous studies using anti-A-MuLV tumor sera (Witte, O. N., Rosenberg, N. and Baltimore, MD. (1979). A normal cell protein cross-reactive to the major Abelson murine leukemia virus gene product. Nature 281, :396–398.), we have detected only one c-abl protein in cells with a normal c-abl gene structure.

In the above examples, the cells and virus which were used are M1-44 which is a clonal lymphoid cell line transformed with the P160 strain of A-MuLV. SCRF60A is a murine thymoma cell line (Lerner, et al., supra). Human leukemia cell lines analyzed included CCRF-CEM (Foley, G. E., Lazarus, H., Farber, S., Uzman, B. G., Boone, B. A. and McCarthy, R. E. (1965). Continuous culture of human lymphoplasts from peripheral blood of a child with acute leukemia. Cancer (Philadelphia) 18, 522–529.), HL-60 (Collins, S. J., Gallo, R. C. and Gallagher, R. E. (1977). Continuous growth and differentiation of human myeloid leukemia cells in suspension culture. Nature 270, 347–349.) and K562 (Lozzio and Lozzio, B. B. (1975). Human chronic myelogenous leukemia cell line with positive Philadelphia chromosome. Blood 45, 321–334.)

Cell labeling and immunoprecipitation was carried out as follows: $2-4 \times 10^7$ exponentially growing cells were washed twice with 150 mM NaCl and then resuspended in 2 ml of the appropriate DMEM minimal media lacking either phosphate or methionine and containing 5% dialyzed fetal calf serum. Labelings were started by the addition of 1 mCi $^{32}$P-orthophosphate (ICN), or 250 micro Ci $^{35}$S-methionine (Amersham) per ml and incubated at 37° C. for 2–4 hrs. The labelings were terminated by washing the cells in phosphate buffered saline. The cells were then extracted into 5 ml of phosphate lysis buffer (PLB) (1% Triton X-100, 0.1% SDS, 0.01M NaH$_2$PO$_4$-Na$_2$HPO$_4$ [pH 7.51]. 0.1M NaCl) with 5 mM EDTA and clarified at 100,000 xg prior to immunoprecipitation. The background resulting from material non-specifically binding to the immune complex required that two cycles of immunoprecipitation be performed in order to confidently detect the c-abl proteins. Therefore, cell extracts were initially immunoprecipitated with 15 microliters αpEX-2 plus 15 microliters pEX-5. Subsequently, the proteins were collected on S. aureus (Kessler, S. W. (1975). Rapid isolation of antigens from cells with a Staphylococcal protein A-antibody adsorbent, J. Immunol. 115, 1617–1624.) eluted with SDS gel sample buffer, and then reprecipitated with appropriate antisera following 10-fold dilution into PLB. The immunoprecipitates were collected on S. aureus and then analyzed by SDS gel electrophoresis (Laemmli, U.K. (1970). Cleavage of structural proteins during the assembly of the head of bacteriophage T4. Nature 277, 680–685.) and autoradiography with an intensifying screen for $^{32}$P-labeled samples. $^{35}$S-labeled samples were detected by fluorography (Chamberlain, J. P. (1979). Fluorographic detection of radioactivity in polyacrylamide gels with the water soluble fluor, sodium salicylate. Anal. Biochem. 98, 132–135.) Molecular weight estimates were made relative to stained molecular weight standards (Sigma) of myosin heavy chain (205 kd), beta-galactosidase (116 kd), phosphorylase B (97.4 kd), bovine serum albumin (66 kd), ovalbumin (45 kd) and carbonic anhydrase (29 kd).

In vitro phosphorylation reactions were conducted as follows: Cell extracts were prepared as described above and then immunoprecipitated with 5 microliters of antisera per one ml of extract overnight. Samples were collected with S. aureus, washed twice with PLB, once with 50 mM Tris pH 7.5, and then resuspended in 40 microliters of 20 mM PIPES (piperazinediethanesulfonate)pH 7.0 with 10 mM MnCl$_2$. Reactions were started by the addition of 5 micro Ci of [$v^{32}$P]ATP (5000 Ci/mmol) (ICN) and then incubated at 30° C. for 5 min. Reactions were terminated by washing the immune complexes twice with PLB plus 5 mM EDTA. The in vitro phosphorylation products were then analyzed by SDS polyacrylamide gel electrophoresis and autoradiography.

The two dimensional phosphopeptide analysis was carried out as follows. $^{32}$P-labeled abl proteins were immunoprecipitated as described above and electrophoresed on SDS polyacrylamide gels. Proteins were localized by autoradiography and cut out of the gel. The proteins were extracted from the gel slices in 50 mM NH$_4$HCO$_3$, 0.1% SDS, 5% 2-mercapto ethanol at 37° for 16 hrs and then precipitated with trichloroacetic acid using 50 micrograms of bovine serum albumins carrier. Samples were prepared for two-dimensional analysis as previously described (Beemon, K. and Hunter, T. (1978). Characterization of Rous sarcoma virus gene products synthesized in vitro. J. Virol. 28, 551–566.) by performic acid oxidation, and digestion with tosyl-L-phenylalanine chloromethyl ketone-trypsin. After concentrating by lyophilization the samples were electrophoresed at 400 V for 1 hr on cellulose thin-layer plates in 1% ammonium carbonate (pH 8.9). Ascending chromatography was performed in the second dimension in n-butanolpyridine-acetic acid-H$_2$O (15–10:3:12). The plates were then autoradiographed with an intensifying screen.

The phosphoamino acid analysis were conducted as follows: Abl proteins labeled in vivo or in vitro were extracted with polyacrylamide gels as described above. The samples were then precipitated with trichloroacetic acid using 50 micrograms of bovine serum albumin as carrier. The pellets were washed twice with cold acetone, dried, and then hydrolyzed for 2 hrs in 100 1 of 6N HCl at 100° C. The hydrolysates were lyophilized, and then resuspended in a mixture of non-radioactively labeled phosphoserine, phosphothreonine, and phosphotyrosine (Sigma). The samples were then electrophoresed on thin layer cellulose plates at pH 3.5 in pyridine-acetic acid-H$_2$O (5:50:945). The plates were stained with ninhydrin to detect the phosphoamino acid standards and were autoradiographed with an intensifying screen to determine the phosphoamino acid composition of the samples.

In accordance with the present invention, when K562 cells which have an altered c-abl gene structure, were analyzed it was found that they express an altered c-abl protein (P210) in addition to the normal sized (P145) c-abl protein. The altered P210 c-abl cross-reacted with abl specific antisera and two-dimensional phosphopeptide analysis indicates P210 is structurally related to the normal P145 human c-abl protein.

As is apparent from the above examples, the P210 protein can function as a marker protein which when detected in a human cell line provides positive identification of CML.

Other CML cell lines were tested for the presence of the P210 protein. The cell lines included EM-2 and EM-3 (see A. Keating, P. J. Martin, I. D. Bernstein, T. PapayannopouLou, W. Raskind, and J. W. Singer (1983). EM-2 and EM-3: Two new Ph[1]+Myeloid Lines. In normal and Neoplastic Hematopoiesis pp 513–520, Alan R. Liss, New York, NY 10011), and BV173 (provided by Dr. Carlo Croce, Wistar Institute, Philadelphia, PA). In each case, the presence of P210 was positively identified. The procedure used for identification was immunoprecipitation of 32-p-orthophosphate labeled cellular extracts and gel electrophoresis analysis.

When v-abl P160 that is phosphorylated in vitro is analyzed for phosphoamino acid composition, virtually all of the covalently bound phosphate is recovered as phosphotyrosine, with a variable and minute amount recovered as phosphoserine. However, analysis of in vitro phosphorylated c-abl P210 revealed that between 15% and 50% of the recovered phosphoamino acids was phosphoserine. The reproducibility of associated serine kinase activity in immunoprecipitates of c-abl P210 is a major difference we have encountered between it and v-abl P160.

Recovery of phosphoserine from in vitro phosphorylated c-abl P210 is not affected by a second cycle of immunoprecipitation following release from the immune complex in SDS gel sample buffer. Thus, one or more serines in c-abl P210 appear to be phosphate-accepting residues for this serine kinase activity. We considered the possibility that the in vitro tyrosine kinase and serine kinase activities of c-abl might be differentially inhibited by anti-pep 5 or anti-pEX 2. Thus, we examined the phosphoamino acid composition of in vitro phosphorylated v-abl P160 and c-abl P210 that had been inhibited by anti-pep 5 or anti-pEX 2 compositions. The phosphoamino acid composition of v-abl P160 that has been inhibited with anti-pep 5 or anti-pEX 2 is similar to the control v-abl P160, the only difference being a trace of phosphoserine. However, the phosphoamino acid composition of c-abl P210 that has been inhibited with anti-pep 5 or anti-pEX 2 is dramatically different from the control c-abl P210. While there is less total phosphoamino acids recovered in anti-pep 5 or anti-peX 2 inhibited c-abl P210, the effect of the inhibition is much greater on recovery of phosphotyrosine than on recovery of phosphoserine. Both kinase inhibitory antisera appear to preferentially block tyrosine kinase activity of c-abl P210. This result suggests that the serine kinase activity of c-abl P210 may be independent of the tyrosine kinase activity. Combined with the fact that v-abl P160 is not always detectably phosphorylated on serine in vitro, this result also suggests that c-abl P210 serine kinase activity may be the result of a separate kinase present in immunoprecipitates that phosphorylates c-abl P210.

We examined the possibility that the serine kinase activity in c-abl P210 immunoprecipitates represents an activity that is not observed for v-abl P160 because of its higher levels of expression and greater tyrosine autokinase activity in immunoprecipitates. Phosphoamino acid analysis of in vitro phosphorylated v-abl P160 prepared from immunoprecipitation of a 1:10 dilution of v-abl P160 into an extract of CCRF-CEM cells (a human leukemia cell line that expresses only normal human c-abl P145) was performed. The in vitro phosphorylated v-abl P160 from the diluted immunoprecipitate had a phosphoamino acid composition containing approximately 10% phosphorserine. In vitro phosphorylated c-abl P210 from a diluted immunoprecipitate prepared in the same way contained more phosphoserine than in a non-diluted immunoprecipitate.

Having thus described exemplary embodiments of the present invention, it should be noted by those skilled in the art that the within disclosues are exemplary only and that various other alternatives, adaptations and modifications may be made within the scope of the present invention. For example, monoclonal antibodies prepared according to standard procedures may be used to separate and identify the P210 protein instead of antibodies prepared as set forth above. Accordingly the present invention is not limited to the specific embodiments as illustrated herein, but is only limited by the following claims.

What is claimed is:

1. A method for detecting chronic myelogenous leukemia in a human comprising the steps of:
    adding an antibody to a biological sample from a human, wherein said antibody specifically binds with c-abl protein having tyrosine kinase activity and a molecular weight of approximately 210,000 to form an immunoprecipitate comprising said antibody bound to said c-abl protein;
    mixing said antibody with said sample for a sufficient time and at a sufficient temperature to allow said antibody to bind to any of said c-abl protein present in said sample to form said immunoprecipitate; and
    detecting chronic myelogenous leukemia by determining whether any of said immunoprecipitate is formed.

2. A method for detecting chronic myelogenous leukemia in a human according to claim 1 wherein said biological sample is bone marrow.

3. A method for detecting chronic myelogenous leukemia according to claim 1 wherein said antibody is prepared according to the steps of:
    incorporating a plasmid which expresses a trp-abl fusion protein into E. coli;
    inducing formation of said fusion protein in said E. coli;
    recovering trp-abl fusion protein from said E. coli;
    administering an immunologically effective amount of said fusion protein to an animal to raise said antibody; and
    isolating said antibody from the immunized animal.

4. A method for detecting chronic myelogenous leukemia according to claim 1 wherein said antibody is prepared according to the steps of:
    coupling a peptide to a non-toxic animal compatible protein carrier to form a peptide-conjugate, said peptide having an amino acid sequence which is the same as a portion of v-abl protein; said sequence including from 11 to 23 amino acids;

administering an immunologically effective amount of said peptide-conjugate to an animal to raise said antibody; and isolating said antibody from the immunized animal.

5. A method for detecting chronic myelogenous leukemia according to claim 1 wherein said antibody is prepared by the steps of:

coupling a peptide to a non-toxic animal compatible protein carrier to form a peptide-conjugate, said peptide having an amino acid sequence which is selected from the group consisting of:

TyrLysGluArgGlyProProAsPGlySerLeu;
TyrLysGlyAlaSerGluAspAspSerArgGluLeu;
TryGluGluAlaAlaGluGluGlyPheLysAspThrGluSerSerProGly
SerSerProProSerLeu;
TyrSerAspGluValGluLysGluLeuGlyLys; and
TyrGlyGluValTyrGluGlyValPheLysLys;

administering an immunologically effective amount of said peptide conjugate to an animal to raise said antibody; and isolating said antibody from the immunized animal.

6. A method for detecting chronic myelogenous leukemia according to claim 4 wherein said non-toxic animal compatible protein is plasma albumin or keyhold limpet hemocyanin.

7. A method according to claim 1 wherein the step of detecting chronic myelogenous leukemia includes the step of separating said immunoprecipitate from said sample by gel electrophoresis.

* * * * *